US012758196B2

(12) United States Patent
Rhodes

(10) Patent No.: US 12,758,196 B2
(45) Date of Patent: Oct. 13, 2026

(54) DYNAMIC RESOURCE RECONFIGURATION FOR PATIENT INTERFACE MODULE (PIM) IN INTRALUMINAL MEDICAL ULTRASOUND IMAGING

(71) Applicant: PHILIPS IMAGE GUIDED THERAPY CORPORATION, San Diego, CA (US)

(72) Inventor: Sidney Rhodes, Roseville, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 0 days.

(21) Appl. No.: 19/218,976

(22) Filed: May 27, 2025

(65) Prior Publication Data

US 2025/0281163 A1 Sep. 11, 2025

Related U.S. Application Data

(63) Continuation of application No. 18/375,664, filed on Oct. 2, 2023, now Pat. No. 12,310,796, which is a (Continued)

(51) Int. Cl.
*A61B 8/00* (2006.01)
*A61B 8/12* (2006.01)
(Continued)

(52) U.S. Cl.
CPC .................. *A61B 8/56* (2013.01); *A61B 8/12* (2013.01); *G16H 30/40* (2018.01); *G16H 80/00* (2018.01); *A61B 8/4483* (2013.01)

(58) Field of Classification Search
CPC .................................... A61B 8/12; A61B 8/54
See application file for complete search history.

(56) References Cited

U.S. PATENT DOCUMENTS 4,917,097 A 4/1990 Proudian
5,368,037 A 11/1994 Eberle
(Continued)

FOREIGN PATENT DOCUMENTS

EP 3335636 A1 6/2018

OTHER PUBLICATIONS

"An Open System for Intravascular Ultrasound Imaging" by W. Qiu et al. IEEE Trans Ultraso Ferro Freq Ctrl. vol. 59, No. 10, pp. 2201-2209, Oct. 2012 (Year: 2012).*
(Continued)

*Primary Examiner* — Jason M Ip

(57) ABSTRACT

Ultrasound image devices, systems, and methods are provided. An intraluminal ultrasound imaging system, comprising a patient interface module (PIM) in communication with an intraluminal imaging device comprising an ultrasound imaging component, the PIM comprising a first reconfigurable logic block including a first plurality of logic elements interconnected by first reconfigurable interconnection elements; a configuration memory coupled to the first reconfigurable logic block; and a processing component coupled to the configuration memory, the processing component configured to detect a device attribute of the intraluminal imaging device in communication with the PIM; and load at least one of a first configuration or a second configuration to the configuration memory based on the detected device attribute to configure one or more of the first reconfigurable interconnection elements such that the first plurality of logic elements are interconnected for communication with the ultrasound imaging component.

9 Claims, 7 Drawing Sheets

Related U.S. Application Data continuation of application No. 16/453,966, filed on Jun. 26, 2019, now Pat. No. 11,771,405.

(60) Provisional application No. 62/690,839, filed on Jun. 27, 2018.

(51) Int. Cl.
*G16H 30/40* (2018.01)
*G16H 80/00* (2018.01)

(56) References Cited

U.S. PATENT DOCUMENTS

| | | | |
|---|---|---|---|
| 5,453,575 A | 9/1995 | O'Donnell | |
| 5,601,082 A | 2/1997 | Barlow | |
| 5,603,327 A | 2/1997 | Eberle | |
| 5,779,644 A | 7/1998 | Eberle | |
| 5,857,974 A | 1/1999 | Eberle | |
| 5,876,344 A | 3/1999 | Baker | |
| 5,921,931 A | 7/1999 | O'Donnell | |
| 5,938,615 A | 8/1999 | O'Donnell | |
| 6,033,357 A | 3/2000 | Ciezki | |
| 6,049,958 A | 4/2000 | Eberle | |
| 6,123,673 A | 9/2000 | Eberle | |
| 6,165,128 A | 12/2000 | Cespedes | |
| 6,283,920 B1 | 9/2001 | Eberle | |
| 6,309,339 B1 | 10/2001 | Cieski | |
| 6,381,350 B1 | 4/2002 | Klingensmith | |
| 6,457,365 B1 | 10/2002 | Stephens | |
| 6,712,767 B2 | 3/2004 | Hossack | |
| 6,725,081 B2 | 4/2004 | Ciezki | |
| 6,767,327 B1 | 7/2004 | Corl | |
| 6,776,763 B2 | 8/2004 | Nix | |
| 6,779,257 B2 | 8/2004 | Kiepen | |
| 6,785,457 B2 | 8/2004 | Mizuuchi | |
| 6,899,682 B2 | 5/2005 | Eberle | |
| 6,962,567 B2 | 11/2005 | Eberle | |
| 6,976,965 B2 | 12/2005 | Corl | |
| 7,097,620 B2 | 8/2006 | Corl | |
| 7,226,417 B1 | 6/2007 | Eberle | |
| 7,641,485 B2 | 1/2010 | Shibata | |
| 7,676,910 B2 | 3/2010 | Kiepen | |
| 7,711,413 B2 | 5/2010 | Feldman | |
| 7,736,317 B2 | 6/2010 | Stephens | |
| 7,846,101 B2 | 12/2010 | Eberle | |
| 2004/0002657 A1 | 1/2004 | Marian | |
| 2010/0324423 A1 | 12/2010 | El-Aklouk | |
| 2013/0303910 A1* | 11/2013 | Hubbard | A61B 8/4461 600/443 |
| 2014/0275844 A1 | 9/2014 | Hoseit | |
| 2015/0133776 A1 | 5/2015 | Hoffman | |
| 2015/0343493 A1 | 12/2015 | Hajati | |
| 2018/0296187 A1 | 10/2018 | Gomersall | |

OTHER PUBLICATIONS

International Search Report and Written Opinion of PCT/EP2019/06811, dated Aug. 5, 2019.

* cited by examiner

DYNAMIC RESOURCE RECONFIGURATION FOR PATIENT INTERFACE MODULE (PIM) IN INTRALUMINAL MEDICAL ULTRASOUND IMAGING

CROSS-REFERENCE TO RELATED APPLICATIONS

The present application is a continuation of U.S. application Ser. No. 18/375,664, filed Oct. 2, 2023, now U.S. Pat. No. 12,310,796, which is a continuation of U.S. application Ser. No. 16/453,966, filed Jun. 26, 2019, now U.S. Pat. No. 11,771,405, which claims priority to and the benefit of U.S. Provisional Application No. 62/690,839, filed Jun. 27, 2018, each of which is incorporated by reference herein in its entirety.

TECHNICAL FIELD

The present disclosure relates generally to intraluminal imaging devices, in particular, to providing a patient interface module (PIM) with reconfigurable hardware resources. For example, a PIM can include a field programmable gate array (FPGA) that can interface and control various intraluminal imaging devices. The FPGA can include reconfigurable logic blocks that can be dynamically reconfigured to communicate with an intraluminal imaging device based on a detection of a device attribute of the intraluminal device.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device including one or more ultrasound transducers is passed into the vessel and guided to the area to be imaged. The transducers emit ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a cross-sectional image of the vessel where the device is placed. IVUS imaging can provide detailed and accurate measurements of lumen and vessel sizes, plaque areas and volumes, and location of key anatomical landmarks. IVUS imaging allows physicians to evaluate the size of a lesion, select a treatment device (e.g., a stent) based on the evaluated lesion size, and subsequently evaluate the treatment success.

There are two types of IVUS catheters commonly in use today: rotational and solid-state. For a typical rotational IVUS catheter, a single ultrasound transducer element is located at the tip of a flexible driveshaft that spins inside a plastic sheath inserted into the vessel of interest. The transducer element is oriented such that the ultrasound beam propagates generally perpendicular to the axis of the device. The fluid-filled sheath protects the vessel tissue from the spinning transducer and driveshaft while permitting ultrasound signals to propagate from the transducer into the tissue and back. As the driveshaft rotates, the transducer is periodically excited with a high voltage pulse to emit a short burst of ultrasound. The same transducer then listens for the returning echoes reflected from various tissue structures. The IVUS imaging system assembles a two dimensional display of the vessel cross-section from a sequence of pulse/acquisition cycles occurring during a single revolution of the transducer.

Solid-state IVUS catheters carry an ultrasound imaging assembly that includes an array of ultrasound transducers distributed around its circumference along with one or more integrated circuit controller chips mounted adjacent to the transducer array. The solid-state IVUS catheters are also referred to as phased array IVUS transducers or phased array IVUS devices. The controllers select individual transducer elements (or groups of elements) for transmitting an ultrasound pulse and for receiving the ultrasound echo signal. By stepping through a sequence of transmit-receive pairs, the solid-state IVUS system can synthesize the effect of a mechanically scanned ultrasound transducer but without moving parts (hence the solid-state designation). Since there is no rotating mechanical element, the transducer array can be placed in direct contact with the blood and vessel tissue with minimal risk of vessel trauma.

Different clinical applications may require different types of IVUS catheters or different imaging modes. In other instances, different types of IVUS catheters or different imaging modes may be required during a clinical procedure. The different types of IVUS catheters may use different communication protocols for communications of commands, statuses, and data. The different communication protocols may use different number of communication signal lines (e.g., wires). The different types of IVUS catheters may communicate analog signals at different voltage levels. The different imaging modes (e.g., including imaging resolution, B-mode imaging, pulse-Doppler, continuous Doppler) may require different trigger signals for ultrasound wave emissions and ultrasound echo receptions.

In an IVUS imaging system, a PIM is typically used to interface a host system with an IVUS catheter. For example, the PIM can coordinate with the host system to control the operation of the IVUS catheter for imaging and the PIM can forward image signals captured by the IVUS catheter to the host system for processing and/or display. Different PIMs may be required for communications with different types of IVUS catheters (e.g., due to different communication protocols) and/or for different imaging procedures (e.g., due to different trigger sequences). One approach to avoid using different PIMs for different types of IVUS catheters may be to include multiple different hardware modules in the PIM to serve different IVUS catheter types and/or different imaging modes. However, such an approach may increase the amount of logics and/or memory resources in a PIM, and thus may lead to a higher cost and may increase the size of the PIM.

SUMMARY

While existing IVUS imaging system have proved useful, there remains a need for improved systems and techniques for real-time system reconfigurations. Embodiments of the present disclosure provide a PIM that includes a field programmable gate array (FPGA) including resources that can be dynamically reconfigured at run-time based on a device attribute of an IVUS catheter attached to the PIM. For example, the resources in the FPGA can be divided into a statically configured portion and a dynamically reconfigurable portion. The statically configured portion can implement functions or operations that are common across multiple different types of intraluminal imaging devices. The dynamically reconfigurable portion can implement functions or operations that are specific to a particular intraluminal imaging device. For example, in the reconfigurable portion, logic cells, logic blocks, and/or logic elements can be dynamically allocated and connection pins can be dynamically assigned to interface to a different IVUS catheter and/or provide a different sequencing algorithm.

In one embodiment, an intraluminal ultrasound imaging system is provided. The system includes a patient interface module (PIM) in communication with an intraluminal imaging device comprising an ultrasound imaging component, the PIM comprising a first reconfigurable logic block including a first plurality of logic elements interconnected by first reconfigurable interconnection elements; a configuration memory coupled to the first reconfigurable logic block; and a processing component coupled to the configuration memory, the processing component configured to: detect a device attribute of the intraluminal imaging device in communication with the PIM; and load at least one of a first configuration or a second configuration to the configuration memory based on the detected device attribute to configure one or more of the first reconfigurable interconnection elements such that the first plurality of logic elements are interconnected for communication with the ultrasound imaging component.

In some embodiments, the processing component is further configured to load the first configuration when the detected device attribute indicates that the intraluminal imaging device comprises a first device attribute; and load the second configuration when the detected device attribute indicates that the intraluminal imaging device comprises a second device attribute, and wherein the first device attribute and the second device attribute are different. In some embodiments, the processing component is further configured to load the first configuration into the configuration memory based on the detection identifying the detected device attribute as the first device attribute. In some embodiments, the first configuration configures the first reconfigurable logic block to establish a digital communication link with the intraluminal imaging device based on a communication protocol associated with the detected device attribute; and transmit, via the digital communication link, a command to configure the intraluminal imaging device. In some embodiments, the first configuration configures the first reconfigurable logic block to establish a digital communication link with the intraluminal imaging device based on a communication protocol associated with the detected device attribute; and receive, via the digital communication link, a status of the intraluminal imaging device. In some embodiments, the first configuration configures the first reconfigurable logic block to receive, from the ultrasound imaging component based on the detected device attribute, an analog signal associated with an ultrasound echo signal received by the ultrasound imaging component, the ultrasound echo signal representative of a subject's body. In some embodiments, the first configuration configures the first reconfigurable logic block to apply a filter to the received analog signal based on the detected device attribute. In some embodiments, the first configuration configures the first reconfigurable logic block to convert the received analog signal to a digital signal based on the detected device attribute. In some embodiments, the PIM further includes a host interface configured to transmit an image signal associated with the ultrasound echo signal to a host. In some embodiments, the ultrasound imaging component includes an array of ultrasound transducers. In some embodiments, the system further comprises a second reconfigurable logic block including a second plurality of logic elements interconnected by second reconfigurable interconnection elements, wherein the processing component is further configured to load a third configuration or a fourth configuration to the configuration memory based on a target imaging mode of an ultrasound imaging procedure to configure the second reconfigurable interconnection elements such that the second plurality of logic elements are interconnected for applying a sequence of trigger signals to the array of ultrasound transducers for ultrasound wave emissions and ultrasound echo receptions. In some embodiments, the PIM further comprises a non-volatile storage memory configured to store the first configuration and the second configuration, and wherein the processing component is further configured to load the at least one of a first configuration or a second configuration to the configuration memory from the non-volatile storage memory. In some embodiments, the system further comprises a field programmable gate array (FPGA) including the first reconfigurable logic block; the configuration memory; and the processing component.

In one embodiment, a method of intraluminal ultrasound imaging is provided. The method includes detecting, by a patient interface module (PIM), a device attribute of an intraluminal imaging device in communication with the PIM, the intraluminal imaging device including an ultrasound imaging component; and loading, by a processing component of the PIM, at least one of a first configuration or a second configuration to a configuration memory of the PIM based on the detected device attribute to configure a first reconfigurable logic block of the PIM, wherein the first reconfigurable logic block includes a first plurality of logic elements interconnected by first reconfigurable interconnection elements, and wherein the first configuration or the second configuration configures one or more of the first reconfigurable interconnection elements such that the first plurality of logic elements are interconnected for communication with the ultrasound imaging component.

In some embodiments, the first configuration is associated with a first device attribute, wherein the second configuration is associated with a second device attribute different from the first device attribute, and wherein the loading includes loading first configuration into the configuration memory based on the detection identifying the detected device attribute including the first device attribute. In some embodiments, the method further comprises establishing, via the first reconfigurable logic block based on the first configuration, a digital communication link with the intraluminal imaging device based on a communication protocol associated with the detected device attribute; and transmitting, via the digital communication link, a command to configure the intraluminal imaging device. In some embodiments, the first configuration configures the first reconfigurable logic block to receive, via the first reconfigurable logic block based on the first configuration, an analog signal associated with an ultrasound echo signal received by the ultrasound imaging component, the ultrasound echo signal representative of a subject's body. In some embodiments, the method further comprises transmitting an image signal associated with the ultrasound echo signal to a host. In some embodiments, the method further comprises loading, by the processing component, a third configuration or a fourth configuration to the configuration memory based on a target imaging mode of an ultrasound imaging procedure to configure a second reconfigurable logic block of the PIM, wherein the second reconfigurable logic block including a second plurality of logic elements interconnected by second reconfigurable interconnection elements, wherein the third configuration or the fourth configuration configures the second reconfigurable interconnection elements such that the second plurality of logic elements are interconnected for applying a sequence of trigger signals to an array of ultrasound transducers of the ultrasound imaging component for ultrasound wave emissions and ultrasound echo receptions. In some embodiments, the loading includes loading the at least one of a first configuration or a second configuration to the configuration memory from a non-volatile storage memory of the PIM.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
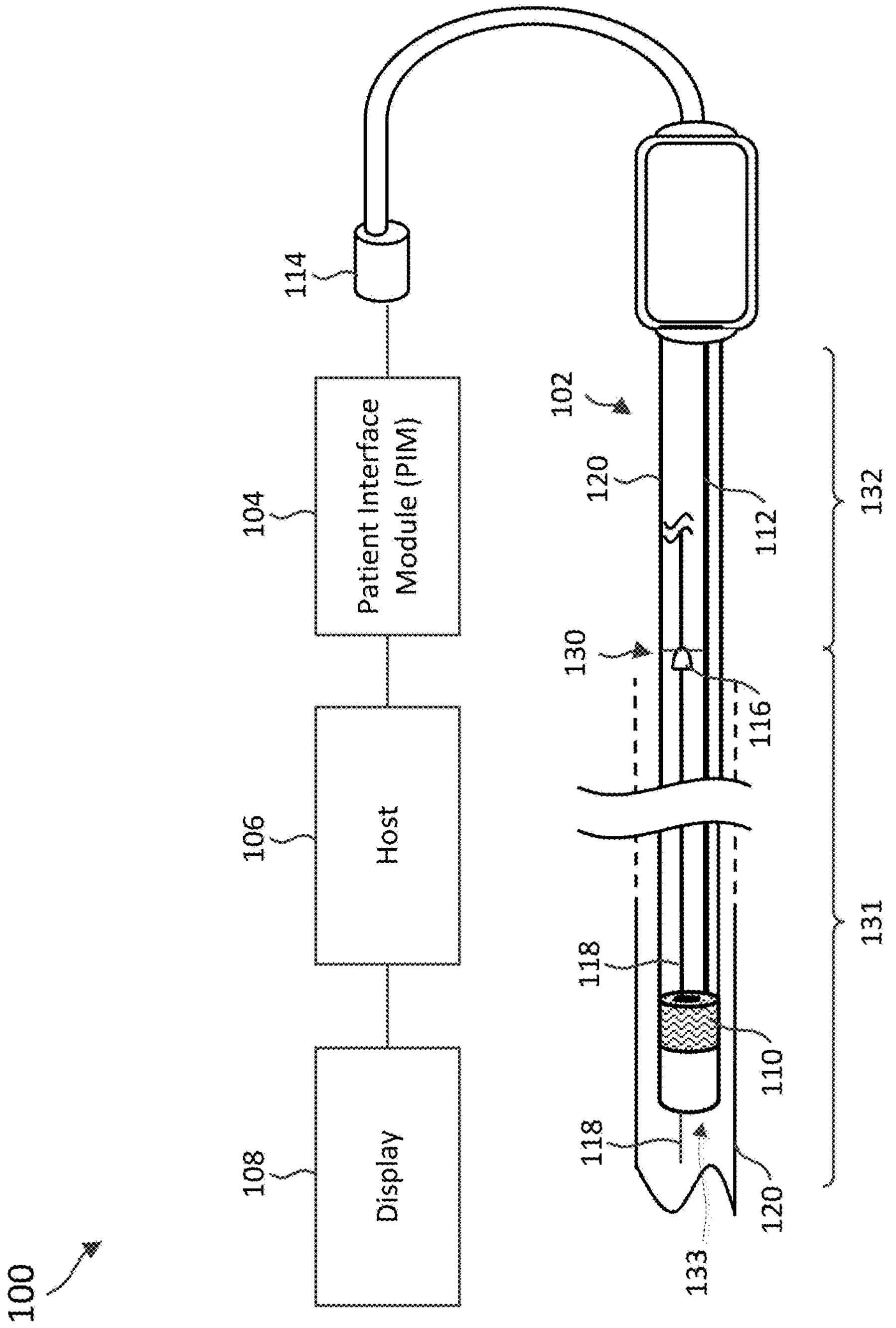
FIG. 1 is a schematic diagram of an intraluminal ultrasound imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a schematic diagram of an intraluminal ultrasound imaging system 100, according to aspects of the present disclosure. The system 100 may include an intraluminal imaging device 102, a patient interface module (PIM) 104, a host system 106, and a display 108. The intraluminal imaging device 102 may be a catheter, a guide wire, or a guide catheter. The intraluminal imaging device 102 can be referred to as an interventional device and/or a diagnostic device, e.g., for use in a medical environment. In some instances, the intraluminal imaging device 102 can be a therapeutic device. The host system 106 may be a console, a computer, a laptop, a tablet, or a mobile device. The display 108 may be a monitor. In some embodiments, the display 108 may be an integrated component of the host system 106.

The intraluminal imaging device 102 may include a flexible elongate member sized and shaped for insertion into the vasculature of a patient. The flexible elongate member may include a distal portion 131 and a proximal portion 132. The intraluminal imaging device 102 may include an imaging component 110 mounted at the distal portion 131 near a distal end 133 of the intraluminal imaging device 102. The intraluminal imaging device 102 may be inserted into a body lumen or vessel 120 of the patient. For example, the intraluminal imaging device 102 can be inserted into a patient's vessel 120 to capture images of the structure of the vessel 120, measure the diameter and/or length of the vessel 120 to guide stent selection, and/or measure blood flow in the vessel 120. The vessel 120 may be any artery or vein within a vascular system of a patient. In some embodiments, the vessel 120 may be a venous vessel, a pulmonary vessel, a coronary vessel, or a peripheral vessel.

In an embodiment, the imaging component 110 may include ultrasound transducers configured to emit ultrasonic energy towards the vessel 120. The emission of the ultrasonic energy may be in the form of pulses. The ultrasonic energy is reflected by tissue structures and/or blood flows in the vessel 120 surrounding the imaging component 110. The reflected ultrasound echo signals are received by the ultrasound transducers in the imaging component 110. In some instances, the imaging component 110 may be configured for brightness-mode (B-mode) imaging to capture images of vessel structures or to measure vessel diameters and lengths for stent selection. In some other instances, the imaging component 110 may be configured for Doppler color flow imaging to provide blood flow measurements. In yet some other instances, the imaging component 110 may be configured to operate in a dual-mode to provide both B-mode imaging data and Doppler flow measurements.

In some embodiments, the ultrasound transducers in the imaging component are phased-array transducers, which may be configured to emit ultrasound energy at a frequency of about 10 megahertz (MHz), 20 MHz, 40 MHz, 45 MHz, and/or other suitable values, both larger and smaller. In some other embodiments, the imaging component 110 may be alternatively configured to include a rotational transducer to provide similar functionalities. The PIM 104 transfers the received echo signals to the host system 106 where the ultrasound image is reconstructed and displayed on the display 108. For example, the strengths or the amplitudes of the echo responses may be converted to brightness or intensity levels for gray-scale image display.

The host system 106 can include a processor and a memory. The host system 106 can be operable to facilitate the features of the system 100 described herein. For example, the processor can execute computer readable instructions stored on the non-transitory tangible computer readable medium.

The PIM 104 facilitates communication of signals between the host system 106 and the intraluminal imaging device 102. This may include forwarding commands received from the host system 106 to the intraluminal imaging device 102 to control the operation of the imaging component 110 and forwarding status reports received from the intraluminal imaging device 102 to the host system 106. In addition, the PIM 104 may generate control signals to configure the imaging component 110, triggering transmitter circuits to cause the imaging component 110 to emit ultrasound waves, and transferring echo signals captured by the imaging component 110 to the host system 106. With regard to the echo signals, the PIM 104 forwards the received signals and, in some embodiments, performs preliminary signal processing prior to transmitting the signals to the host 106. In examples of such embodiments, the PIM 104 performs amplification, filtering, and/or aggregating of the data. In an embodiment, the PIM 104 also supplies high- and low-voltage direct current (DC) power to support operation of the circuitry within the imaging component 110. Mechanisms for triggering the transmitter circuits are described in greater detail herein.

In an embodiment, the host system 106 receives the echo data from the imaging component 110 and/or transmits controls to the imaging component 110 by way of the PIM 104. The host system 106 processes the echo data to reconstruct an image of the tissue structures in the vessel 120 surrounding imaging component 110. The host system 106 outputs image data such that an image of the vessel 120, such as a cross-sectional image of the vessel 120, is displayed on the display 108.

In some embodiments, the intraluminal imaging device 102 includes some features similar to traditional solid-state IVUS catheters, such as the EagleEye® Platinum, Eagle Eye® Platinum ST, Eagle Eye® Gold, and Visions® PV catheters available from Volcano Corporation and those disclosed in U.S. Pat. No. 7,846,101 hereby incorporated by reference in its entirety. For example, the intraluminal imaging device 102 further includes an electrical cable 112 extending along the longitudinal body of the intraluminal imaging device 102. The cable 112 is a transmission line bundle including a plurality of conductors, including one, two, three, four, five, six, seven, or more conductors. It is understood that any suitable gauge wire can be used for the conductors. In an embodiment, the cable 112 can include a four-conductor transmission line arrangement with, e.g., 41 American wire gauge (AWG) wires. In an embodiment, the cable 112 can include a seven-conductor transmission line arrangement utilizing, e.g., 44 AWG wires. In some embodiments, 43 AWG wires can be used. In some other embodiments, the intraluminal imaging device 102 includes some features similar to traditional rotational IVUS catheters, such as the Revolution® catheter available from Volcano Corporation and those disclosed in U.S. Pat. Nos. 5,601,082 and 6,381,350, each of which is hereby incorporated by reference in its entirety. In some embodiments, the intraluminal imaging device 102 includes components or features similar or identical to those disclosed in U.S. Pat. Nos. 4,917,097, 5,368,037, 5,453,575, 5,603,327, 5,779,644, 5,857,974, 5,876,344, 5,921,931, 5,938,615, 6,049,958, 6,0854,109, 6,123,673, 6,165,128, 6,283,920, 6,309,339; 6,033,357, 6,457,365, 6,712,767, 6,725,081, 6,767,327, 6,776,763, 6,779,257, 6,7854,157, 6,899,682, 6,962,567, 6,976,965, 7,097,620, 7,226,417, 7,641,4854, 7,676,910, 7,711,413, and 7,736,317, each of which is hereby incorporated by reference in its entirety.

The cable 112 terminates in a PIM connector 114 at a proximal end of the intraluminal imaging device 102. The PIM connector 114 electrically couples the cable 112 to the PIM 104 and physically couples the intraluminal imaging device 102 to the PIM 104. In an embodiment, the intraluminal imaging device 102 further includes a guide wire exit port 116 disposed near a junction 130 at which the distal portion 131 is coupled to the proximal portion 132. Accordingly, in some instances the intraluminal imaging device 102 is a rapid-exchange catheter. The guide wire exit port 116 allows a guide wire 118 to be inserted towards the distal end 133 in order to direct the intraluminal imaging device 102 through the vessel 120.

Different clinical or imaging applications may require the use of different types of intraluminal imaging devices 102, which may have different dimensions and/or different imaging capabilities. For example, imaging of peripheral vessels, imaging of coronary vessels, measurements of blood flow, and evaluations of vascular morphology in blood vessels may each require a particular type of intraluminal imaging device 102. Different types of intraluminal imaging devices 102 (e.g., the EagleEye® Platinum, Eagle Eye® Platinum ST, Eagle Eye® Gold, Visions® PV, and/or Revolution® catheters available from Volcano Corporation) may communicate information (e.g., commands and statuses) using different number of physical signal lines, for example, to carry data, controls, addresses, and/or clock signals. In addition, the encoding of the data may be different depending on the communication protocols. For example, some intraluminal devices 102 may use a serial communication interface while other intraluminal devices 102 may use an inter-integrated circuit (I2C) interface. Further, the different types of intraluminal imaging devices 102 may require different trigger signals to control ultrasound wave emissions and/or ultrasound echo signals receptions at the imaging component 110. For example, trigger signals for a phased-array imaging component 110 may be different from trigger signals for a rotational-based imaging component 110.

Different clinical or imaging applications may use different imaging modes to acquire different type of diagnostic information (e.g., B-mode data and color Doppler flow data). Different ultrasound center frequencies may be used to compromise signal penetration depths and image resolutions. For example, the imaging component 110 may be configured to emit ultrasound waves at a higher center frequency to provide a higher imaging resolution, trading off penetration depth. Conversely, the imaging component 110 may be configured to emit ultrasound waves at a lower center frequency to provide a deeper penetration, trading off imaging resolution. Thus, different trigger signals may be required to trigger ultrasound transmit pulses of different center frequencies.

Different ultrasound pulse durations may be used for obtaining different imaging views. For example, the imaging component 110 may be configured to emit ultrasound pulses with a shorter duration, but at a higher signal energy level. For example, higher-energy ultrasound waves can be used during color flow imaging to provide a better view of blood vessel boundaries. Alternatively, higher-energy ultrasound waves can be used to provide a larger field-of-view during peripheral imaging due to the larger peripheral vessel sizes, for example, when capturing an image of an aorta artery during abdominal imaging or an iliac artery during limb imaging. Thus, different trigger signals may be required to trigger ultrasound transmit pulses of different durations and/or different energy levels.

As can be seen, different intraluminal imaging devices 102 may require different number of physical signal lines and communication protocols for data and/or signal transfers. In addition, different imaging components 110 and/or different target imaging modes may require trigger signals of different waveform characteristics (e.g., voltage levels, frequencies, and/or duty cycles) and of different trigger sequences. In an embodiment, the PIM 104 may include reconfigurable hardware resources that can be dynamically reconfigured in run-time based on an attached intraluminal imaging device 102. For example, the PIM 104 can detect a device attribute (e.g., a device type and/or an ultrasound attribute) of the attached intraluminal imaging device 102 and configure the reconfigurable hardware resources accordingly. Mechanisms for dynamic hardware resource reconfiguration in the PIM 104 are described in greater detail herein.

Figure 2:
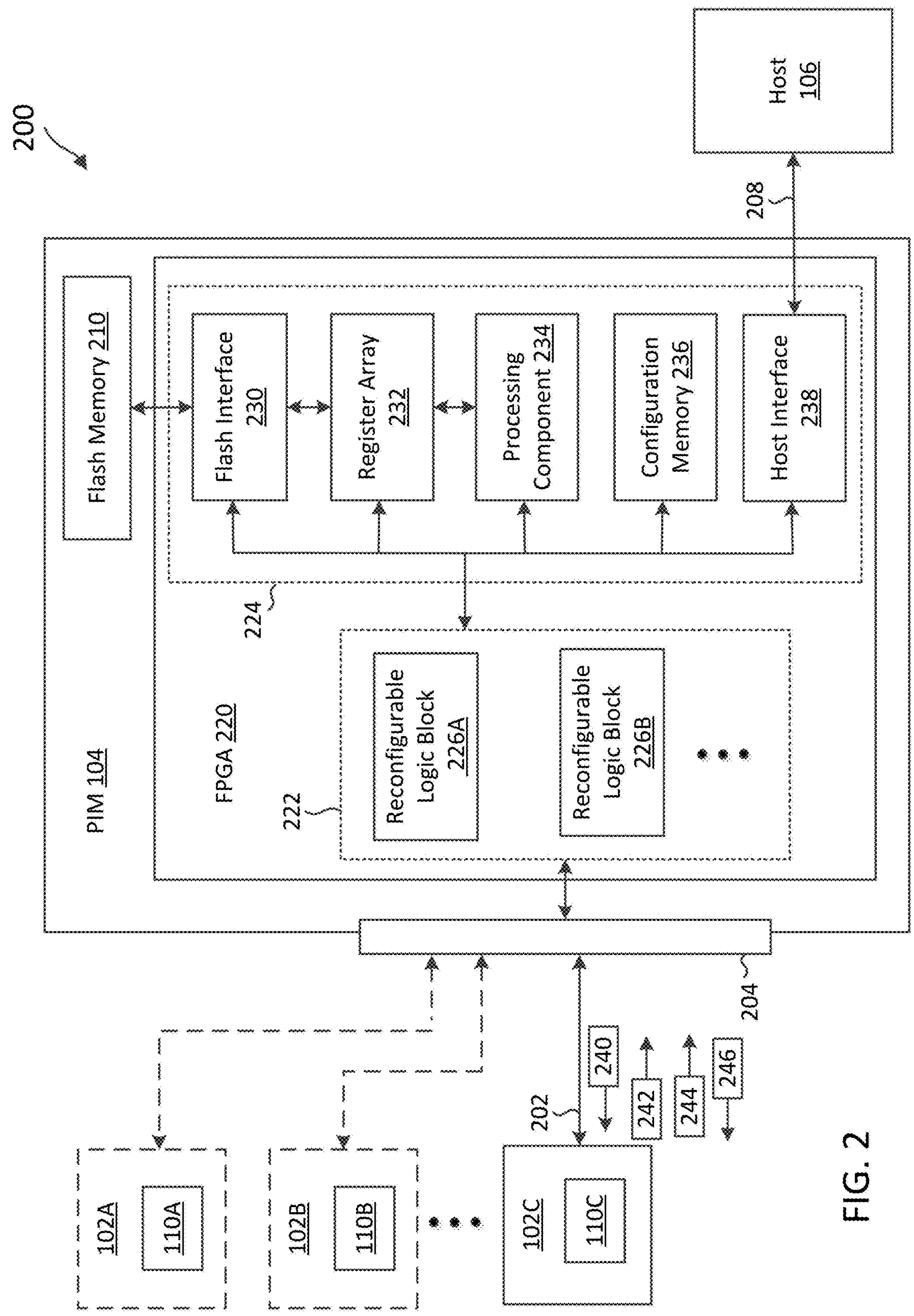
FIG. 2 is a schematic diagram illustrating a system configuration for an intraluminal ultrasound imaging system, according to aspects of the present disclosure.
Figure 3:
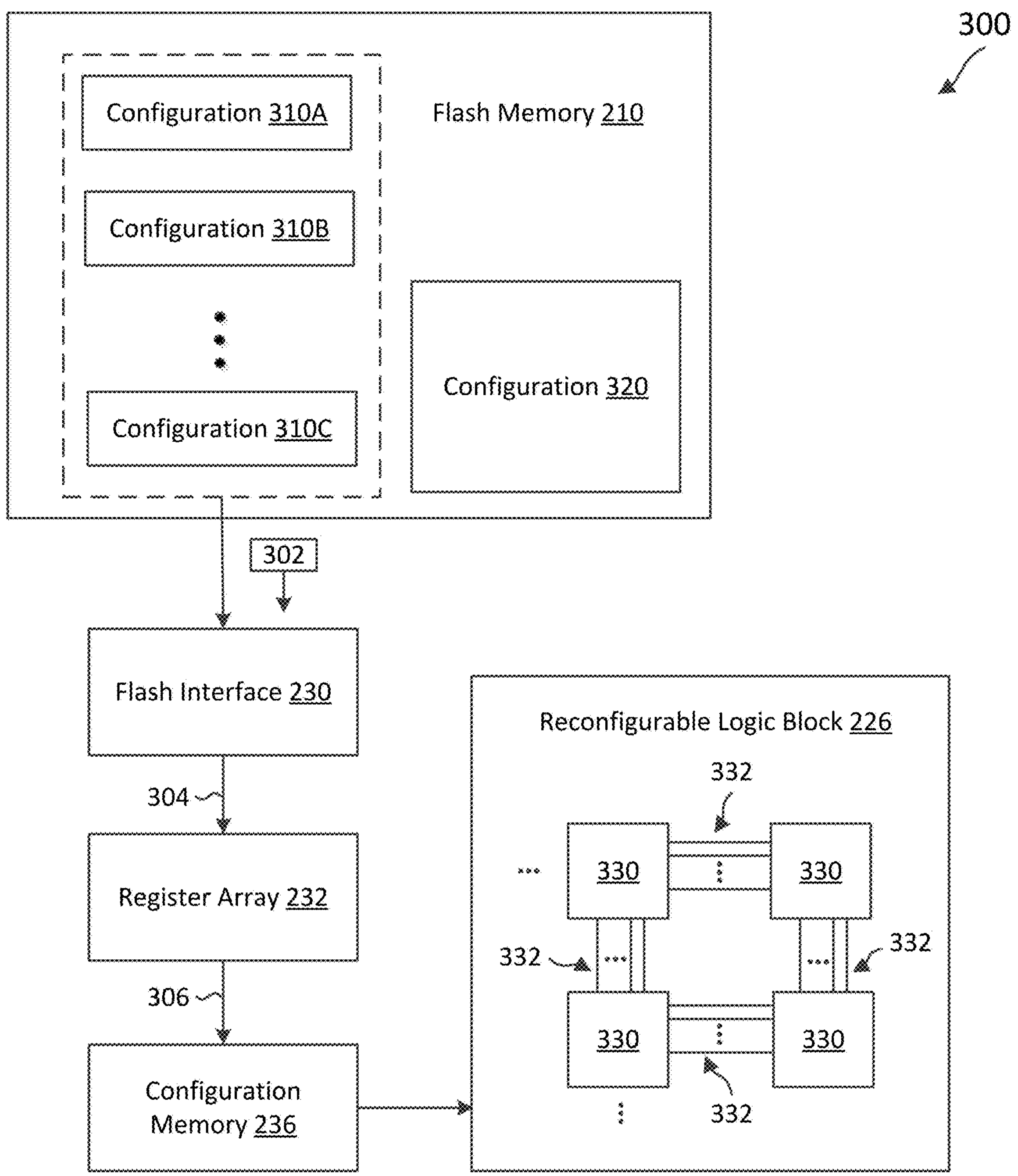
FIG. 3 is a schematic diagram illustrating a dynamic resource reconfiguration scheme for a patient interface module (PIM), according to aspects of the present disclosure.

FIG. 2 is a schematic diagram illustrating a system configuration 200 for the intraluminal ultrasound imaging system 100, according to aspects of the present disclosure. FIG. 2 provides a more detailed view of the internal components of the PIM 104 and interactions among the PIM 104, the host 106, and the intraluminal imaging device 102 in communication with the PIM 104. FIG. 3 is a schematic diagram illustrating a dynamic resource reconfiguration scheme 300 for the PIM 104, according to aspects of the present disclosure. As shown in FIG. 2, the PIM 104 includes a device connector 204 coupled to an FPGA 220. At a high level, upon an attachment of an intraluminal imaging device 102 to the device connector 204, the PIM 104 can detect and identify a device attribute of the attached intraluminal imaging device 102. The PIM 104 can load a configuration bitstream onto the FPGA 220 at run-time to configure the FPGA 220 for communication with the attached intraluminal imaging device 102.

The device connector 204 may be a common intraluminal imaging device connector suitable for coupling with various different intraluminal imaging devices 102. The device connector 204 may include digital signal connections and analog signal connections coupled to an attached intraluminal imaging device 102 via a link 202. The intraluminal imaging devices are shown as 102A, 102B, and 102C. As an example, the intraluminal imaging device 102A may be a rotational IVUS catheter including an imaging component 110A with a single ultrasound transducer element. The intraluminal imaging device 102B may be a solid-state IVUS catheter, for example, suitable for coronary imaging. The intraluminal imaging device 102C may include an imaging component 110C with phased-array ultrasound transducers. The intraluminal imaging device 102C may be another solid-state IVUS catheter, for example, suitable for peripheral imaging. The intraluminal imaging device 102C may include an imaging component 110C with phased-array ultrasound transducers.

The different intraluminal imaging devices 102A, 102B, and 102C may have different dimensions and/or different number of physical signal lines for communications. For example, the intraluminal device 102A may communicate with the PIM 104 over four physical signal lines, while the intraluminal devices 102B and 102C may communicate with the PIM 104 over six physical signal lines. In some other instances, the different intraluminal imaging devices 102A, 102B, and 102C may have the same number of physical signal lines, but may have different pin assignments for connections to the device connector 204.

The different intraluminal imaging devices 102A, 102B, and 102C may employ different communication protocols for digital communications and/or different voltage levels for transfer of analog and/or digital signals. For example, the intraluminal imaging device 102A may employ an I2C communication protocol, while the intraluminal imaging device 102B may employ a high-speed I2C communication protocol. In some instances, a digital signal for the intraluminal device 102A may carry a 7-bit address field, an 8-bit data field, and 3 groups of 4-bit controls, while a digital signal for the intraluminal device 102B and 102C may carry a 3-bit address field, an 8-bit data field, and a 3-bit control field. In some instances, the intraluminal imaging device 102A may communicate using differential signals, while the intraluminal device 102B may communicate using common-mode signals.

The different intraluminal imaging devices 102A, 102B, and 102C may have different imaging capabilities, such as different ultrasound center frequencies and/or different imaging cores (e.g., a phased-array or a rotational imaging core). The imaging components 110A, 110B, and 110C may require different trigger signals for ultrasound wave emissions and/or ultrasound echo receptions. For example, the imaging components 110A, 110B, and 110C may be designed to emit ultrasound waves with different center frequencies. In some embodiments, each intraluminal imaging device 102 may include a non-volatile memory configured to store device information, such as a serial number, a device identification number, a catheter type, and other device attributes (e.g., ultrasound attributes and/or a physiological sensing modality) related to a corresponding ultrasound imaging component 110.

The FPGA 220 includes programmable fabric in the form of configurable logic cells or logic elements (e.g., logic elements 330 shown in FIG. 3) and configurable switches or interconnection elements (e.g., interconnection elements 332 shown in FIG. 3). The logic elements may include multipliers, adders, flip-flops, and/or other logic gates. The configurable interconnection elements can be configured to interconnect the logic elements to provide a desired function (e.g., implementing a particular communication protocol or a particular sequence of operations). The configurable logic elements and configurable interconnection elements can be divided into two portions, a dynamically reconfigurable portion 222 and a statically configured portion 224.

The statically configured portion 224 may implement modules or logic blocks that are common across the intraluminal imaging devices 102. As shown, the statically configured portion 224 includes a flash interface 230, a register array 232, a processing component 234, a configuration memory 236, and a host interface 238. The dynamically reconfigurable portion 222 may implement modules or logic blocks that are specific to an intraluminal imaging device 102 (e.g., the intraluminal imaging device 102C) attached to the PIM 104. As shown, the dynamically reconfigurable portion 222 includes a plurality of reconfigurable logic blocks 226. The reconfigurable logic blocks 226A and 226B can be reconfigured at run-time for communication with the attached intraluminal imaging device 102 as described in greater detail herein.

The flash interface 230 is configured to communicate with an external flash memory. For example, the PIM 104 can further include a flash memory 210. The flash memory 210 is a non-volatile memory, such as a flash memory card. The flash memory 210 is configured to store configuration data, which may be referred to as FPGA configuration bitstreams. The flash memory 210 can store partial configuration bitstreams. As shown in FIG. 3, the flash memory 210 stores a plurality of configuration data 310 and a configuration data 320. The configuration data 320 defines the locations and the switching of the interconnection elements in the statically configured portion 224. For example, the configuration data 320 configures the statically configured portion 224 to implement the register array 232, the processing component 234, the configuration memory 236, and the host interface 238.

The configuration data 310 defines the locations and switching of the interconnection elements in the dynamically reconfigured portion 222. Each configuration data 310 is associated with a specific attribute of an intraluminal imaging device 102. As an example, the configuration data 310A defines the locations and switching of the interconnection elements in the reconfigurable logic blocks 226A and 226B to implement a communication interface and a sequencer (e.g., for generating transmit/receive trigger signals) specific to the intraluminal imaging device 102A. The configuration data 310B defines the locations and switching of the interconnection elements in the reconfigurable logic blocks 226A and 226B to implement a communication interface and a sequencer specific to the intraluminal imaging device 102B. The configuration data 310C defines the locations and switching of the interconnection elements in the reconfigurable logic blocks 226A and 226B to implement a communication interface and a sequencer specific to the intraluminal imaging device 102C, as described in greater detail herein.

The processing component 234 is coupled to the flash interface 230 and the register array 232. The processing component 234 can be any type of central processing unit (CPU). In some instances, the processing component 234 can be a microcontroller, a general purpose processor (GPU), or a digital signal processor (DSP). The processing component 234 is configured to detect a device attribute of an intraluminal imaging device 102 attached to the PIM 104. The device attribute can include a communication protocol (e.g., I2C, a high-speed I2C, or a serial communication link) used by the attached intraluminal imaging device 102 for communication. The device attribute can include an ultrasound attribute of the imaging component 110 of the intraluminal imaging device 102. The ultrasound attribute may include an operational center frequency (e.g., of about 10 MHz, 20 MHz, 40 MHz, 45 MHz, and/or other suitable values, both larger and smaller) of the imaging component 110. In addition, the ultrasound attribute may indicate an imaging core type of the imaging component 110, for example, whether the imaging component 110 is a phased-array ultrasound imaging component or a rotational ultrasound imaging component.

The processing component 234 can select a configuration from the plurality of configuration data 310 based on the detected device attribute. The processing component 234 can configure the dynamically reconfigurable portion 222 of FPGA 220 based on the detected device attribute. As shown in FIG. 3, the processing component 234 can load the selected configuration data 302 via the flash interface 230 and the register array 232 into the configuration memory 236. The configuration memory 236 and the register array 232 can be any random access memory (RAM). For example, the selected configuration data 302 is received at the register array 232 as shown by the arrow 304. The configuration data 302 is transferred from the register array 232 into the configuration memory 234 as shown by the arrow 306. The configuration data 302 stored in the configuration memory 234 is used to configure the interconnection elements 332 to interconnect the logic elements 330 in a reconfigurable logic block 226, for example, to implement a communication interface or a sequencer for the attached intraluminal imaging device 102. The configuration data 310 are referred to as a partial FPGA bitstream. In some embodiments, the processing component 234 can form a full FPGA bitstream including the configuration data 320 (e.g., static or common among intraluminal imaging devices 102) and the selected configuration data 302 (e.g., the configuration data 310C) and load the full FPGA bitstream into the configuration memory 234. While FIG. 3 illustrates four logic elements 330 for simplicity of discussion, the reconfigurable logic block 226 can be scaled to include any suitable number of logic elements 330.

In some embodiments, the FPGA 220 can further include a device detection logic block that can detect an attachment of an intraluminal imaging device 102 to the PIM 104 and notify the processing component 234 of the detection.

The host interface 238 may include hardware components and/or software components configured to communicate with the host 106 via a link 208. In some instances, the communication link 208 may be a wired connection, such as an Ethernet link, a universal serial bus (USB) link, or any suitable wired communication link. In other instances, the link 208 may be a wireless link, such as an Institute of Electrical and Electronics Engineers (IEEE) 802.11 (WiFi) link, a Bluetooth link, a Zigbee link, or an ultra-wideband (UWB) link. The host interface 238 can be coupled to the reconfigurable logic blocks 226. For example, the host 106 can send commands to the attached intraluminal imaging device 102 and receive echo signals or image signals via the host interface 238 and the reconfigurable logic blocks 226.

As an example, when the intraluminal imaging device 102A is connected to the PIM 104, the processing component 234 can automatically identify a device attribute of the intraluminal imaging device 102A. The processing component 234 can load the configuration data 310A into the configuration memory 236 to dynamically reconfigure the reconfigurable logic blocks 226 in run-time to implement at least a communication interface for communicating with the intraluminal imaging device 102A and a sequencer for controlling the imaging component 110A. After the reconfigurable logic blocks 226 are configured, the reconfigurable logic block 226A functions as an analog interface and/or a digital interface for communicating with the intraluminal imaging device 102A. For example, the PIM 104 can send commands 240 (e.g., reset, restart, and/or stop) to the imaging component 110A and can receive statuses 242 (e.g., high-voltage (HV) out of range and/or sensor element failures) from the imaging component 110A via the reconfigurable logic blocks 226. The reconfigurable logic block 226A can also receive ultrasound echo signals 244 captured by the imaging component 110A. The reconfigurable logic block 226B functions as a sequencer to generate a sequence of trigger signals 246 to control ultrasound wave emissions and ultrasound echo receptions at the imaging component 110A. The trigger signals 246 may include one or more trigger signals for activating ultrasound wave emissions and/or one or more trigger signals for activating ultrasound echo receptions.

Alternatively, when the intraluminal imaging device 102B is connected to the PIM 104, the processing component 234 can automatically identify a device attribute of the intraluminal imaging device 102B. The processing component 234 can load the configuration data 310B into the configuration memory 236 to dynamically reconfigure the reconfigurable logic blocks 226 in run-time to implement at least a communication interface for communicating with the intraluminal imaging device 102B and a sequencer for controlling the imaging component 110B. After the reconfigurable logic blocks 226 are configured, the reconfigurable blocks 226A and 226B can provide similar functionalities as described above, but specific to the intraluminal imaging device 102B.

While FIGS. 2 and 3 illustrate a single configuration data 310 for reconfiguring the dynamically reconfigurable portion 222 of the FPGA 220, in some embodiments, the configuration data for the interface and the configuration data for the sequencer can be stored as separate configuration data 310.

Figure 4:
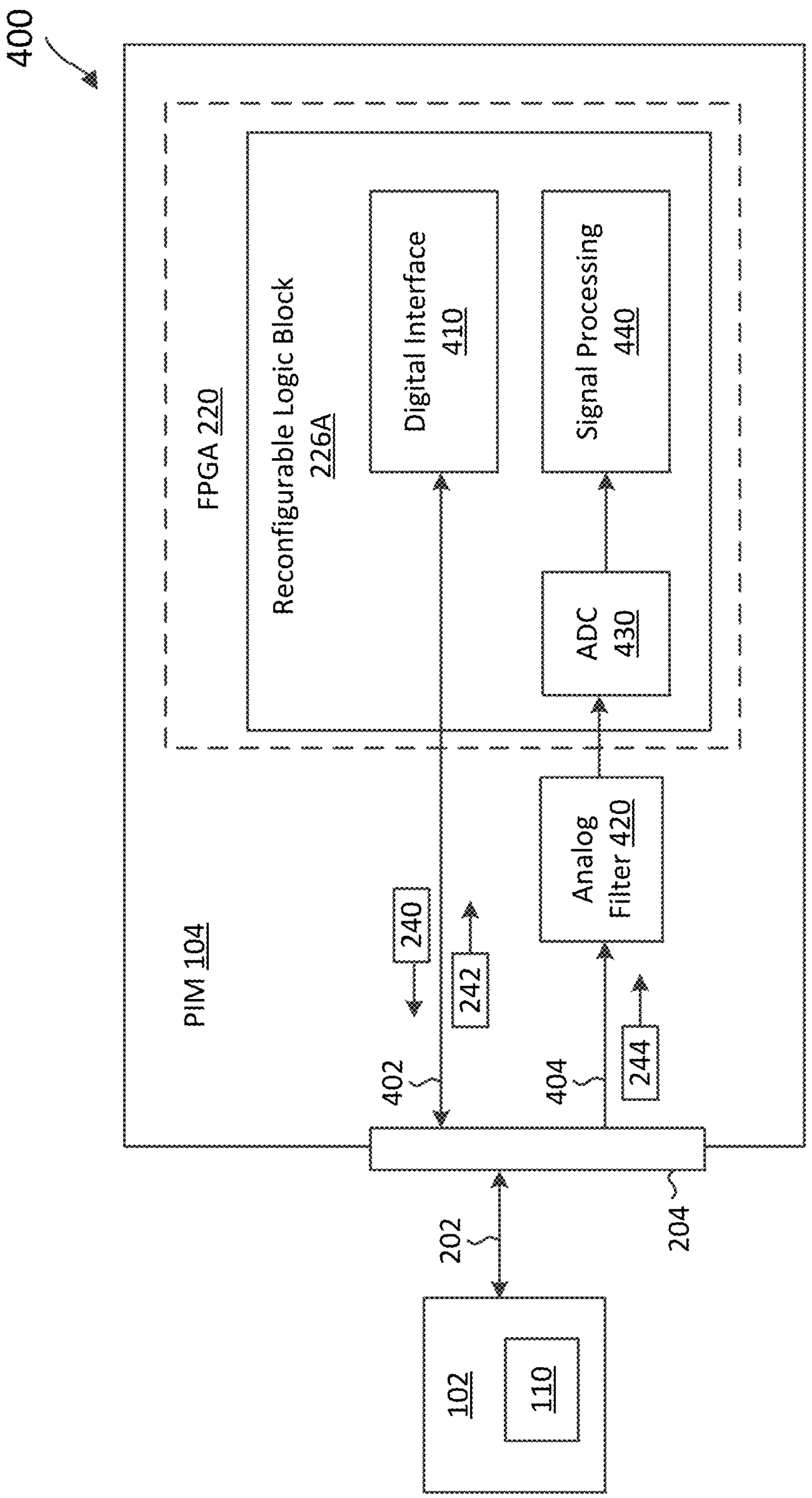
FIG. 4 is a schematic diagram illustrating a device interface configuration for a PIM, according to aspects of the present disclosure.

FIG. 4 is a schematic diagram illustrating a device interface configuration 400 for the PIM 104, according to aspects of the present disclosure. The configuration 400 provides a more detailed view of an example of a reconfigurable logic block 226A configured to function as a communication interface for communicating with an intraluminal imaging device 102. FIG. 4 illustrates the interface portion of the PIM 104 for simplicity of discussion, but may include other logic blocks as described above with respect to FIGS. 2 and 3. As shown, the interface includes a digital path 402 and an analog path 404. The digital path 402 is coupled to a digital interface block 410. The analog path 404 is coupled to an analog filter 420, an analog-to-digital converter (ADC) 430, and a signal processing block 440. The digital interface block 410, the ADC 430, and the signal processing block 440 can be implemented by the reconfigurable logic block 226A. While FIG. 4 illustrates one analog filter 420 and one ADC 430, the PIM 104 may include any suitable number of analog filters 420 and ADCSs 430.

As described above, the PIM 104 can exchange commands 240 and statuses 242 with an attached intraluminal imaging device 102. The commands 240 and the statuses 242 can be communicated over the digital path 402. The digital interface block 410 can be configured to implement a communication protocol (e.g., I2C, high-speed I2C, or any serial communication scheme) of the attached intraluminal imaging device 102C. The communication protocol may include specific voltage levels, signal types, and/or data coding schemes.

The PIM 104 can also receive ultrasound echo signals 244 captured by the imaging component 110 of the attached intraluminal imaging device 102. The echo signals 224 can be transferred over the analog path 404. The echo signals 244 are analog radio frequency (RF) signals. The analog filter 420 can condition a received echo signal 244. The ADC 430 can convert an analog signal to a digital signal for subsequent digital signal processing. In some instances, the analog filter 420 may be an antialiasing filter for the ADC 430. The analog filter 420 can be a band pass filter, where the filter characteristics (e.g., the 3 decibel (dB) roll-off and bandwidth) may be dependent on the bandwidth of the ultrasound echo signal 244, the center frequency of an ultrasound wave emission that causes the echo signal 244, and/or a sampling rate of the ADC 430. The signal processing block 440 can perform preprocessing to condition the echo signal 244 for further image processing. In some embodiments, the signal processing block 440 can include a digital filter (e.g., a notch filter) specific to the imaging component 110 of the attached intraluminal imaging device 102. In some embodiments, the signal processing block 440 can implement an envelope detection algorithm and/or a logarithmic compressions algorithm for B-mode processing. In some embodiments, the signal processing block 440 can implement an image analysis algorithm (e.g., boundary detection and/or blood flow estimation). In some embodiments, the analog path 404 can further include an analog amplifier for amplifying the received echo signal 244 and/or other mixer circuitry for converting the RF echo signal 244 into a baseband signal prior to the ADC 430. In some embodiments, the ADC 430 can be an ADC external to the FPGA 220.

Figure 5:
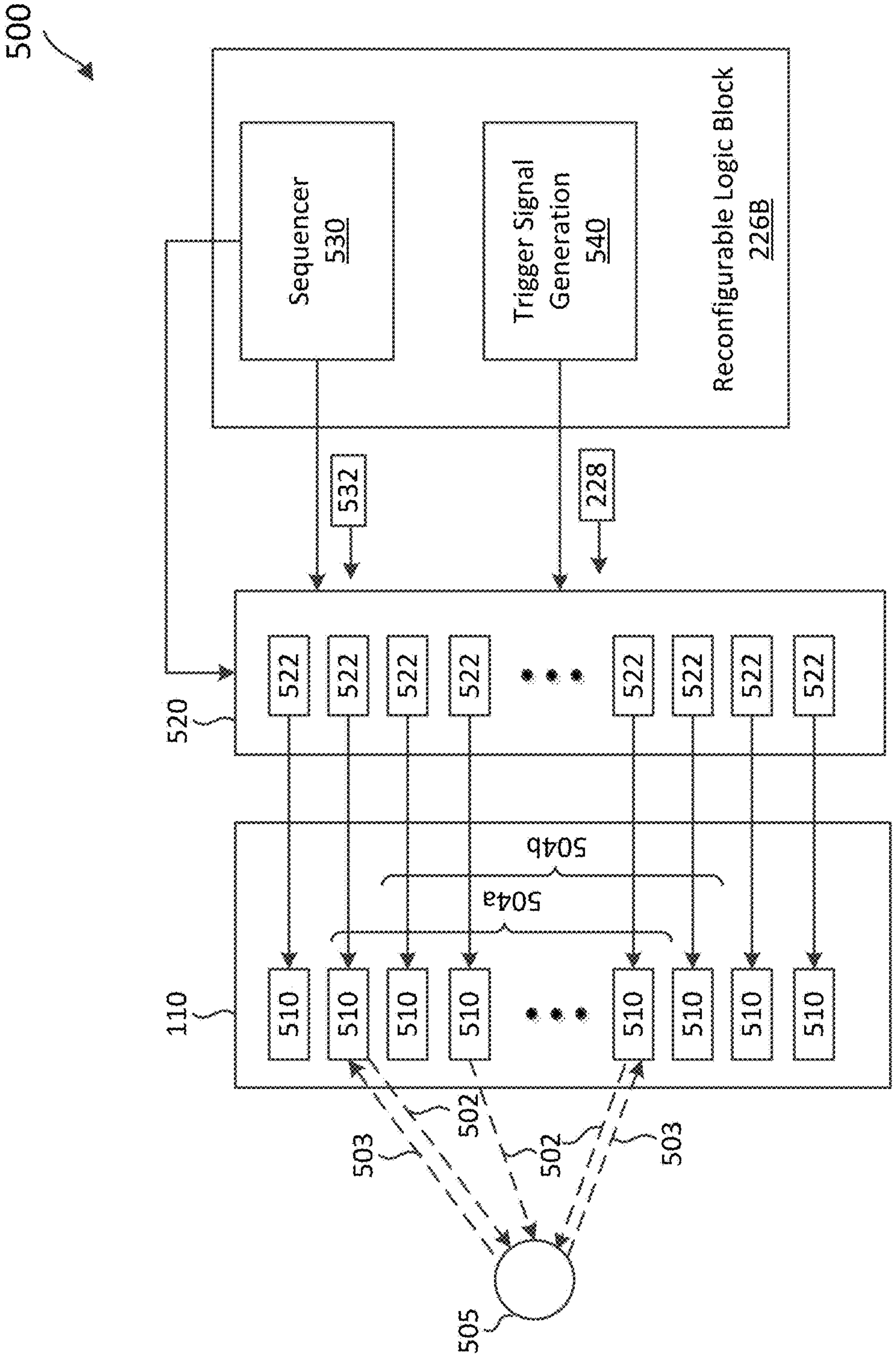
FIG. 5 is a schematic diagram illustrating an ultrasound imaging configuration, according to aspects of the present disclosure.

FIG. 5 is a schematic diagram illustrating an ultrasound imaging configuration 500, according to aspects of the present disclosure. The configuration 500 provides a more detailed view of an example of a reconfigurable logic block 226B configured to function as a sequencer for controlling ultrasound wave emissions and ultrasound echo receptions at an imaging component 110 of an attached intraluminal imaging device 102. For example, the reconfigurable logic block 226B can control transmit and/or receive triggers to provide synthetic aperture ultrasound imaging. The configuration 500 includes a multiplexer 520 coupled to the imaging component 110, a sequencer block 530, and a trigger signal generation block 540. The imaging component 110 may correspond to an imaging component 110C of the intraluminal imaging device 102C attached to the PIM 104 shown in FIG. 2. The imaging component 110 may include an array of ultrasound transducers 510. The sequencer block 530 and the trigger signal generation block 540 can be implemented by the reconfigurable logic block 226B.

The multiplexer 520 may include a plurality of transmit switching circuitries 522. Each transmit switching circuitry 522 may be coupled to one of the transducers 510. Each transmit switching circuitry 522 may include a driver that can activate ultrasound wave emissions at transducers 510 and a switch that can gate or allow an electrical signal (e.g., a trigger signal 246) to pass through to a corresponding transducer 510.

The sequencer block 530 controls the timing and the sequence of activations at the transducers 510 (e.g., for emitting ultrasound waves) and the trigger signal generation block 540 generates trigger signals to activate the transducers 510 based on a detected device attribute or ultrasound attribute of the imaging component 110. The transmit switching circuitries 522 in the multiplexer 520 may receive trigger signals 246 from the trigger signal generation block 540 and send the trigger signals 228 through to the transducers 510 according to the timing and sequence provided by the sequencer block 530. For example, the sequencer block 530 may provide a timing sequence 532 indicating a sequence (e.g., including an order and timing) for firing a set of transducers 510.

In some embodiments, the transducers 510 may be grouped into apertures 504, including apertures 504*a* and 504*b*. In some embodiments, each transducer 510 may be part of one or more apertures 504. Each aperture 504 may include any suitable number of transducers 510. The sequencer block 530 may activate one or more transducers 510 in an aperture 504 to emit ultrasound waves 502 (e.g., ultrasound transmit pulses). The ultrasound waves 502 may be emitted towards a target anatomical structure 505 (e.g., a blood vessel). While not shown in FIG. 5, the configuration 500 may further include receive switching circuitries coupled to the transducer so that the sequencer block 530 may also activate one or more transducers 510 in the aperture 504 to receive echo signals 503 reflected back from the structure 505. The received echo signals 503 may create an A-line in an image representing the structure 505.

While the multiplexer 520 is illustrated with a separate transmit switching circuitry 522 for each transducer 510, the transmit switching circuitries 522 can be configured in any suitable configuration, for example, some transducers 510 may be coupled to the same transmit switching circuitry 522. In addition, in some embodiments, the sequencer block 530 may be coupled to the trigger signal generation block 540 and the trigger signal generation block 540 can apply encoded trigger signals to the imaging component 110. The encoded trigger signals can further include information indicating the transducers 510 selected by the sequencer block 530

Figure 6:
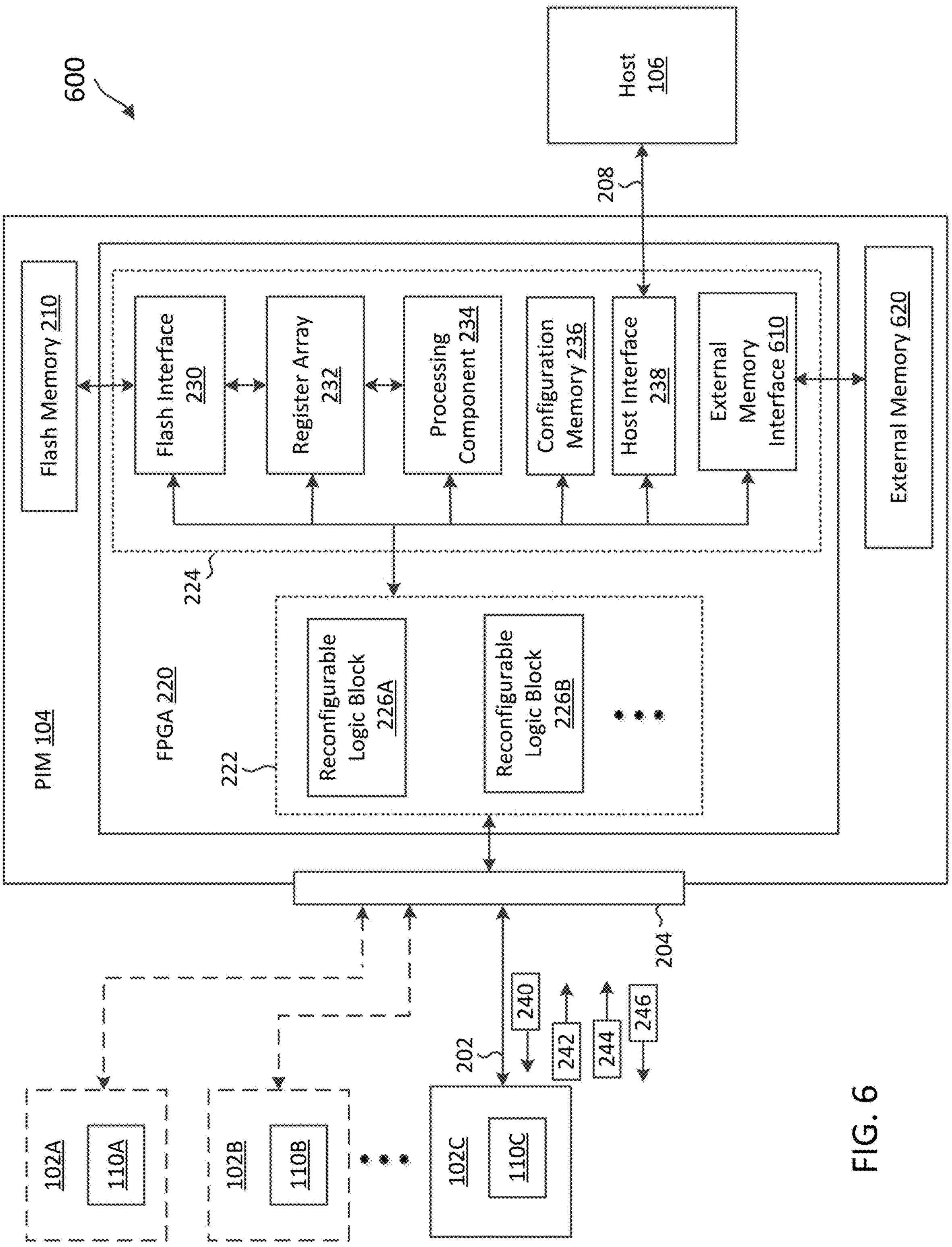
FIG. 6 is a schematic diagram illustrating a system configuration for an intraluminal ultrasound imaging system, according to aspects of the present disclosure.

FIG. 6 is a schematic diagram illustrating a system configuration 600 for the intraluminal ultrasound imaging system 100, according to aspects of the present disclosure. The system configuration 600 may be substantially similar to the system configuration 200. For example, the PIM 104 can detect an attachment of an intraluminal imaging device 102C, identify a device attribute of the attached intraluminal imaging device 102, and dynamically configure the dynamically reconfigurable portion 222 of the FPGA 220. However, in the system configuration 600, the PIM 104 may include an additional memory 620 external to the FPGA 220 and statically configured portion 224 can include an additional external memory interface 610. The memory 620 can be any RAM and may include a large storage size (e.g., a few megabytes to a few gigabytes). The external memory interface 610 may be coupled to the internal blocks of the FPGA 220 and may provide an interface for the FPGA 220 to read from the memory 620 or write to the memory 620. For example, the signal processing block 440 can implement more complex signal processing and/or image processing algorithms, such beamforming or focusing algorithms. The complex algorithms may require additional memory for storing working data. The working data can be transferred to the memory 620 via the external memory interface 610.

Figure 7:
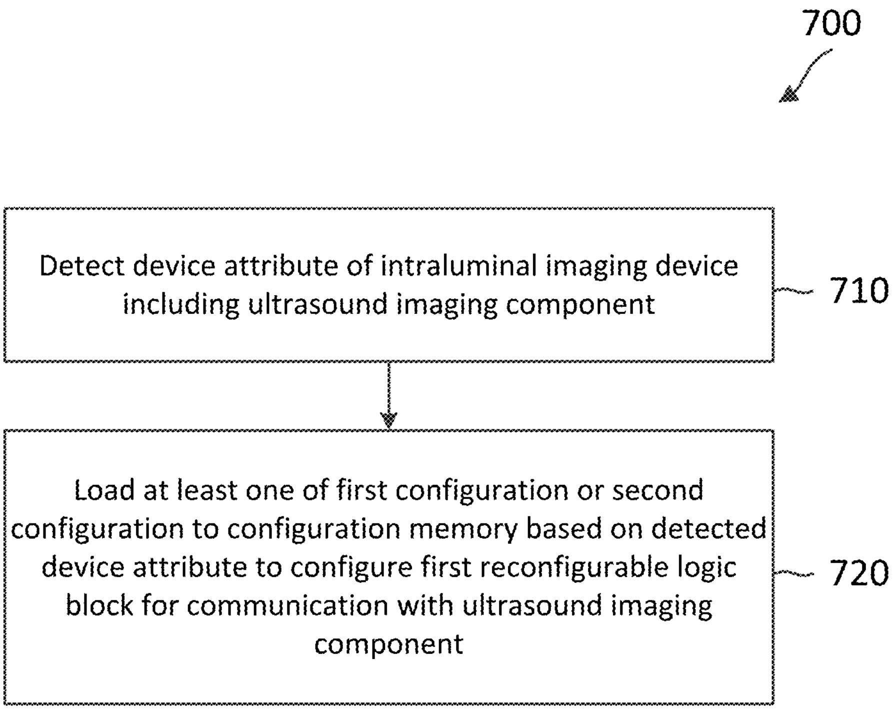
FIG. 7 is a flow diagram of a method of ultrasound imaging, according to aspects of the disclosure.

FIG. 7 is a flow diagram of a method 700 of ultrasound imaging, according to aspects of the disclosure. Steps of the method 700 can be executed by the system 100. The method 700 may employ similar mechanisms as in the system configurations 200, 400, 500, and 600 and the scheme 300 as described with respect to FIGS. 2, 4, 5, 6, and 3, respectively. As illustrated, the method 700 includes a number of enumerated steps, but embodiments of the method 700 may include additional steps before, after, and in between the enumerated steps. In some embodiments, one or more of the enumerated steps may be omitted or performed in a different order.

At step 710, the method includes detecting, by a PIM (e.g., the PIM 104), a device attribute of an intraluminal imaging device (e.g., the intraluminal imaging device 102) in communication with the PIM, the intraluminal imaging device including an ultrasound imaging component (e.g., the imaging component 110). The device attribute can include information associated with a communication protocol, a signal type (e.g., differential or common-mode), and/or a voltage level used by the intraluminal imaging device for communications and/or an ultrasound attribute (e.g., a center frequency, an imaging core such as a phased-array or a rotational core) of the imaging component.

At step 720, the method 700 includes loading, by a processing component (e.g., the processing component 234) of the PIM, at least one of a first configuration (e.g., the configuration data 310A) or a second configuration (e.g., the configuration data B) to a configuration memory (e.g., the configuration memory 236) of the PIM based on the detected device attribute to configure a first reconfigurable logic block (e.g., the reconfigurable logic blocks 226A) of the PIM. The first reconfigurable logic block includes a first plurality of logic elements (e.g., the logic elements 330) interconnected by first reconfigurable interconnection elements (e.g., the interconnection elements 332). The first configuration or the second configuration configures one or more of the first reconfigurable interconnection elements such that the first plurality of logic elements are interconnected for communication with the ultrasound imaging component.

In some embodiments, the first configuration is associated with a first device attribute and the second configuration is associated with a second device attribute different from the first device attribute. The loading includes loading first configuration into the configuration memory based on the detection identifying the detected device attribute including the first device attribute. In some instances, the first configuration is loaded from a non-volatile storage memory (e.g., the flash memory 210) of the PIM.

In some embodiments, the method 700 can include establishing, via the first reconfigurable logic block based on the first configuration, a digital communication link (e.g., the digital path 402) with the intraluminal imaging device based on a communication protocol associated with the detected device attribute. The PIM can transmit, via the digital communication link, a command (e.g., the commands 240) to configure the intraluminal imaging device.

In some embodiments, the first configuration can configure the first reconfigurable logic block to receive, via the first reconfigurable logic block based on the first configuration, an analog signal associated with an ultrasound echo signal (e.g., the echo signal 244) received by the ultrasound imaging component. The ultrasound echo signal representative of a subject's body (e.g., the vessel 120 or the structure 305). The method 700 can further include transmitting an image signal associated with the ultrasound echo signal to a host (e.g., the host 106).

In some embodiments, the method 700 can include loading, by the processing component, a third configuration or a fourth configuration to the configuration memory based on a target imaging mode (e.g., B-mode or Color Doppler mode) of an ultrasound imaging procedure to configure a second reconfigurable logic block (e.g., the reconfigurable logic block 226B) of the PIM. The second reconfigurable logic block includes a second plurality of logic elements interconnected by second reconfigurable interconnection elements. The third configuration or the fourth configuration can configure the second reconfigurable interconnection elements such that the second plurality of logic elements are interconnected for applying a sequence of trigger signals to an array of ultrasound transducers (e.g., the transducers 510) of the ultrasound imaging component for ultrasound wave emissions (e.g., the ultrasound waves 502) and ultrasound echo receptions (e.g., the ultrasound echo signals 503).

Aspects of the present disclosure can provide several benefits. For example, the automatic detection of a device attribute of an intraluminal ultrasound imaging device 102 upon attachment to the PIM 104 can allow the PIM 104 to reconfigure the resources for communicating and/or controlling the attached intraluminal ultrasound imaging device 102 in run-time. Thus, the PIM 104 is not required to include resources for multiple different combinations of implementations for supporting different types of intraluminal imaging devices. As such, the dynamic reconfiguration of resources enables the PIM 104 to have a small footprint and a low cost. The dynamic resource configuration also enables the implementation of complex algorithms based on the intraluminal imaging device in use, rather than unnecessarily occupying resources while using another intraluminal imaging device. For example, the reconfigurable logic blocks can be configured to implement different sequencing algorithms based on the intraluminal imaging device in use and the desired diagnostic information.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intravascular ultrasound (IVUS) imaging system, comprising:
- an IVUS imaging catheter configured to be positioned inside a blood vessel and comprising one or more ultrasound transducers; and
- a patient interface module (PIM) comprising a field programmable gate array (FPGA),
- wherein the FPGA itself is configured to operate as a trigger signal generator for B-mode imaging of the blood vessel and color flow imaging of the blood vessel,
- wherein, when the FPGA operates as the trigger signal generator for the B-mode imaging of the blood vessel, the FPGA is configured to generate a first trigger signal to cause the one or more ultrasound transducers to emit, for B-mode imaging, ultrasound transmit pulses with a first energy level and a first duration,
- wherein, when the FPGA operates as the trigger signal generator for the color flow imaging, the FPGA is configured to generate a different, second trigger signal to cause the one or more ultrasound transducers to emit, for the color flow imaging, ultrasound transmit pulses with a second energy level higher than the first energy level and a second duration shorter than the first duration.

2. The system of claim 1, wherein the FPGA comprises one or more dynamically reconfigurable portions that are reconfigurable to operate as the trigger signal generator for the B-mode imaging or as the trigger signal generator for the color flow imaging.

3. The system of claim 2, wherein the PIM is configured to:
- select a first configuration for the one or more dynamically reconfigurable portions to operate as the trigger signal generator for the B-mode imaging or a second configuration for the one or more dynamically reconfigurable portions to operate as the trigger signal generator for the color flow imaging.

4. The system of claim 3,
- wherein the FPGA comprises a plurality of interconnection elements and a plurality of logic elements,
- wherein, to reconfigure the one or more dynamically reconfigurable portions, the PIM is configured to change how the plurality of interconnection elements provide interconnection for the plurality of logic elements.

5. The system of claim 4, wherein the first configuration or the second configuration define how the plurality of interconnection elements provide the interconnection for the plurality of logic elements.

6. The system of claim 3,
- wherein the PIM comprises a first memory configured to store the first configuration and the second configuration,
- wherein the first memory is distinct from the FPGA.

7. The system of claim 6,
- wherein the FPGA comprises a statically configured portion,
- wherein the statically configured portion comprises a processor and a second memory,
- wherein the processor is configured to load the first configuration or the second configuration into the second memory.

8. The system of claim 1, further comprising a host configured to:
- generate a circumferential image of the blood vessel based on at least one of the B-mode imaging or the color flow imaging; and
- output the circumferential image of the blood vessel to a display.

9. The system of claim 1, wherein the one or more ultrasound transducers comprise a rotational transducer or a transducer array.

* * * * *